United States Patent [19]

Rowlands et al.

[11] 4,151,280

[45] Apr. 24, 1979

[54] PYRROLOQUINOXALINES

[75] Inventors: David A. Rowlands, Cirencester; John B. Taylor, Crucis near Cirencester, both of England

[73] Assignee: Roussel Uclaf, Paris, France

[21] Appl. No.: 895,264

[22] Filed: Apr. 10, 1978

[30] Foreign Application Priority Data

Apr. 13, 1977 [GB] United Kingdom ............... 15350/77

[51] Int. Cl.$^2$ ................. C07D 487/04; A61K 31/495
[52] U.S. Cl. .................................. 424/250; 544/344; 548/333
[58] Field of Search .......................... 544/344; 424/250

[56] References Cited
PUBLICATIONS

Ogaru et al., J. Org. Chem. 37, pp. 2679–2682, (1972).
Kumashiro et al., Chem. Abs. 57, 12489, (1961).

*Primary Examiner*—Mark L. Berch
*Attorney, Agent, or Firm*—Hammond & Littell

[57] ABSTRACT

Novel pyrroloquinoxalines of the formula

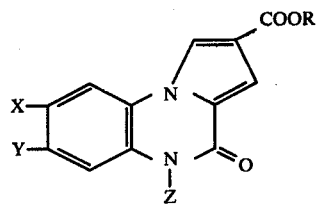

wherein X and Y are individually selected from the group consisting of hydrogen, halogen, alkyl and alkoxy of 1 to 5 carbon atoms and $-NO_2$, Z is selected from the group consisting of alkyl of 1 to 8 carbon atoms, cycloalkyl of 3 to 8 carbon atoms, alkenyl of 2 to 6 carbon atoms and phenyl and R is selected from the group consisting of hydrogen, alkyl of 1 to 5 carbon atoms,

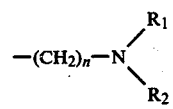

and non-toxic, pharmaceutically acceptable cations, n is an integer from 1 to 6 and $R_1$ and $R_2$ are individually alkyl of 1 to 5 carbon atoms and the non-toxic, pharmaceutically acceptable acid addition salts thereof having antiallergic activity and to a novel process for their preparation.

27 Claims, No Drawings

PYRROLOQUINOXALINES

STATE OF THE ART

Copending, commonly assigned U.S. Patent Application Ser. No. 799,580 now abandoned filed May 23, 1977 describes imidazobenzoxazines having antiallergic and bronchodilatory activity and copending, commonly assigned U.S. patent application Ser. No. 869,842 filed Jan. 16, 1978 describes imidazoquinolines having the same activity. Ogura et al [J. Org. Chem., Vol. 37, No. 17 (1972), p. 2679–2682] describes the reaction of a 1-Z-benzimidazole with an alkyl haloacetate but they do not appear to have isolated any product of formula I therefrom.

OBJECTS OF THE INVENTION

It is an object of the invention to provide the novel pyrroloquinoxalines of formula I and a novel process for their preparation.

It is another object of the invention to provide novel antiallergic compositions and to provide a novel method of treating allergy in warm-blooded animals.

These and other objects and advantages of the invention will become obvious from the following detailed description.

THE INVENTION

The novel pyrroloquinoxalines of the invention have the formula

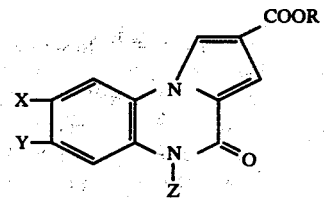

wherein X and Y are individually selected from the group consisting of hydrogen, halogen, alkyl and alkoxy of 1 to 5 carbon atoms and $-NO_2$, Z is selected from the group consisting of alkyl of 1 to 8 carbon atoms, cycloalkyl of 3 to 8 carbon atoms, alkenyl of 2 to 6 carbon atoms and phenyl and R is selected from the group consisting of hydrogen, alkyl of 1 to 5 carbon atoms,

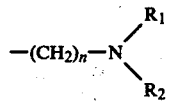

and non-toxic, pharmaceutically acceptable cations, n is an integer from 1 to 6 and $R_1$ and $R_2$ are individually alkyl of 1 to 5 carbon atoms and the non-toxic, pharmaceutically acceptable acid addition salts thereof.

The alkyl and alkoxy groups may be straight chain or branched chain. Examples of X and Y are hydrogen, chlorine, bromine, methyl, methoxy and nitro. Examples of Z are alkyl such as methyl, ethyl, propyl, isopropyl, n-butyl, isobutyl, pentyl, hexyl, heptyl and octyl; cycloalkyl such as cyclopropyl, cyclobutyl, cyclopentyl and cyclohexyl; and alkenyl such as allyl, but-2-en-1-yl and pent-2-en-1-yl.

Examples of R are alkyl such as methyl, ethyl, propyl, isopropyl, butyl, sec-butyl, tert.-butyl and pentyl;

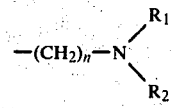

where $R_1$ and $R_2$ are individually alkyl such as methyl, ethyl, propyl, isopropyl, butyl and pentyl; and cations such as alkali metals like sodium, potassium and lithium, alkaline earth metals like calcium, the magnesium, the aluminum, the ammonium and the non-toxic pharmaceutically acceptable organic amines like lysine, arginine, triethanolamine and tris(hydroxymethyl)-aminomethane.

Examples of suitable acids for the non-toxic, pharmaceutically acceptable acid addition salts are inorganic acids like hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid, tartaric acid, citric acid, oxalic acid, glyoxalic acid, aspartic acid, alkanesulfonic acids such as methanesulfonic acid and arylsulfonic acids such as benzenesulfonic acid.

Among the preferred compounds of formula I are those wherein Z is selected from the group consisting of alkyl of 1 to 8 carbon atoms, cyclopentyl, allyl and phenyl and R is hydrogen or alkyl of 1 to 5 carbon atoms and those wherein X and Y are individually selected from the group consisting of hydrogen, chlorine and nitro and Z is alkyl of 1 to 5 carbon atoms, cyclopentyl, allyl and phenyl and those wherein R is hydrogen and Z is alkyl of 1 to 5 carbon atoms.

Specific preferred compounds of formula I are 5-methyl-4,5-dihydro-4-oxo-pyrrolo[1,2-a]quinoxaline-2-carboxylic acid, 5-ethyl-4,5-dihydro-4-oxo-pyrrolo[1,2-a]quinoxaline-2-carboxylic acid, 5-n-propyl-4,5-dihydro-4-oxo-pyrrolo [1,2-a]quinoxaline-2-carboxylic acid, 5-n-butyl-4,5-dihydro-4-oxo-pyrrolo[1,2-a]quinoxaline-2-carboxylic acid, 8-chloro-5-n-butyl-4,5-dihydro-4-oxo-pyrrolo[1,2-a]quinoxaline-2-carboxylic acid, 7,8-dichloro-5-n-butyl-4,5-dihydro-4-oxopyrrolo[1,2-a]quinoxaline-2-carboxylic acid and the nontoxic, pharmaceutically acceptable salts thereof.

The novel process of the invention for the preparation of compounds of formula I wherein R is other than hydrogen or a cation comprises reacting under basic conditions a compound of the formula

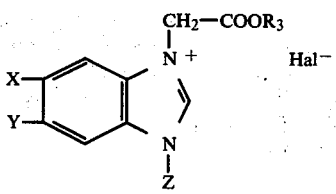

wherein X, Y and Z have the above definitions and $R_3$ is alkyl of 1 to 5 carbon atoms and Hal is a halogen such as chlorine or bromine with a compound of the formula $CH \equiv C - COOR'$ wherein $R'$ is selected from the group consisting of alkyl of 1 to 5 carbon atoms and

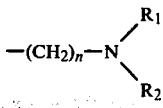

wherein n, $R_1$ and $R_2$ have the above definitions. The reaction is preferably effected in an organic solvent such as dimethylformamide in the presence of a base such as alkali metal carbonates like potassium carbonate or sodium carbonate or an organic amine such as triethylamine.

The compounds of formula IV may be formed by a process analogous to that of Ogura et al [J. Org. Chem., Vol. 37, No. 17 (1972), p. 2679–2682] by reacting a compound of the formula

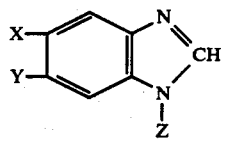

II with a compound of the formula

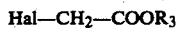

III in the presence of an organic solvent such as benzene or ether.

The process of the invention for the preparation of compounds of formula I wherein R is hydrogen comprises hydrolyzing a compound of formula I wherein R is other than hydrogen or a cation in the presence of a base such as alkali metal hydroxides such as sodium hydroxide or potassium hydroxide.

The compounds of formula I wherein R is other than hydrogen or a cation may also be prepared by reacting a compound of formula I wherein R is hydrogen or a reactive derivative thereof with a compound of the formula HOR' wherein R' has the above definition or a reactive derivative thereof. The acid halide of formula I may be prepared, for example, by reaction with thionyl chloride and the acid chloride may be reacted with HOR' in the presence of an acid binding agent such as triethylamine. The said esterification is preferably effected in an anhydrous solvent such as dichloromethane or diethyl ether.

The compounds of formula I may be reacted with a substantially equimolar amount of an acid to form the corresponding acid addition salt thereof and when R is hydrogen, the compound may be reacted with a substantially equimolar amount of the desired organic or inorganic base to form the salt thereof.

Certain of the compounds of formula II, useful as starting materials in the preparation of compounds of formula I are known in the literature. Compounds of formula II wherein Z is alkyl of 1 to 8 carbon atoms, a cycloalkyl of 3 to 8 carbon atoms or an alkenyl of 2 to 6 carbon atoms may be obtained, for example, by reaction of a compound of the formula.

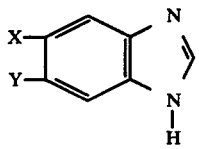

IV wherein X and Y are as hereinbefore defined with a compound of the formula

VII wherein Z' is alkyl of 1 to 8 carbon atoms, cycloalkyl of 3 to 8 carbon atoms or alkenyl of 2 to 6 carbon atoms and Hal' is a halogen atom such as chlorine, bromine or iodine.

When X and Y are not identical, such a reaction may, in some cases, give a mixture of products monoalkylated on either of the two amino groups and the mixed monoalkyl products may be separated at this stage or it may be more convenient to react the mixture as described above to form a mixture of acids of formula I (R=H) which may more readily be separated. The invention thus extends to the foregoing reactions carried out with mixed starting materials to give products which may then, if desired, be subjected to separation. On the other hand, under certain reaction conditions, the reaction product of formula II may consist of virtually a single isomer. Thus, for example, reaction of 5-chlorobenzimidazole with diethyl sulfate by the method of Aliprandi [Ann. Chim. (Rome) 1958, Vol. 48, p. 1349–56] produces 1-ethyl-5-chloro-benzimidazole in high yield, whereas reaction of 5-chloro-benzimidazole with 1-bromo-butane in ethanolic potassium hydroxide gave 1-ethyl-6-chloro-benzimidazole.

Compounds of formula II wherein Z is a phenyl may be prepared, for example, by reaction of a compound of the formula

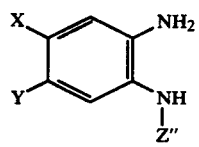

VIII wherein X and Y are as hereinbefore defined and Z" is a phenyl with formic acid in the presence of concentrated hydrochloric acid. The compounds of formula II wherein Z is a group other than phenyl may also be prepared if desired, by an analogous method using a compound of formula VIII wherein Z" represents an appropriate radical.

The compound of formula VIII wherein Z" has any of the meanings given above for Z may, for example, be prepared by reduction, e.g. by catalytic hydrogenation, of a compound of the formula

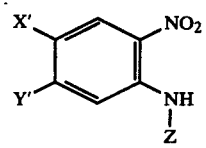

IX wherein X' and Y' have the meanings given above for X and Y respectively with the exception of nitro and Z has the above meanings. Compounds of formula IX may be prepared by reaction of a compound of the formula

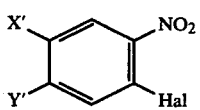

X wherein X', Y' and Hal have the above meanings, with an amine of the formula $NH_2Z$ where Z has the above meaning.

The novel antiallergic compositions of the invention are comprised of an antiallergically effective amount of at least one compound. of formula I and their non-toxic, pharmaceutically acceptable acid addition salts and an inert pharmaceutical carrier or excipient. The compositions may be in the form of tablets, coated tablets, gelatin capsules, granules, suppositories, syrups, aerosols, creams, ointments and injectable solutions or suspensions.

Examples of suitable excipients are talc, gum arabic, lactose, starch, magnesium stearate, cacao butter, aqueous and non-aqueous vehicles, fatty substances of animal or vegetable origin, paraffinic derivatives, glycols, preservaties and diverse wetting agents, dispersants and emulsifiers.

The compositions due to their antiallergic activity are useful for the treatment of asthma and bronchial asthma of an allergic origin.

The novel method of the invention for inducing antiallergic activity in warm-blooded animals comprises administering to warm-blooded animals an antiallergically effective amount of at least one compound of formula I and their non-toxic, pharmaceutically acceptable acid addition salts. The compounds may be administered orally, rectally, parenterally or topically. The usual useful dose is 0.005 to 2 mg/kg depending on the compound and the administration method.

In the following examples there are described several preferred embodiments to illustrate the invention. However, it is to be understood that the invention is not intended to be limited to the specific embodiments.

EXAMPLE 1 ethyl 5-methyl-4,5-dihydro-4-oxo-pyrrolo[1,2-a]quinoxaline-2-carboxylate

STEP A: 1-methyl-benzimidazole 14.1 g of methyl iodide and 6.15 g of potassium hydroxide were added to a suspension of 11.8 g of benzimidazole in 50 ml of ethanol and 30 ml of water and the mixture was refluxed for 6 hours and was then cooled. The mixture was extracted three times with chloroform and the combined chloroform extracts were dried and filtered. The filtrate was evaporated to dryness and the oily residue was chromatographed over neutral alumina. Elution with chloroform yielded 1-methyl-benzimidazole as a crude oil which was used as is for the next step.

STEP B: 1-ethoxycarbonylmethyl-3-methyl-benzimidazolium bromide

The 1-methyl-benzimidazole of Step A was dissolved in ether and 1.4 equivalents of ethyl bromoacetate were added thereto. The ether solution was allowed to stand for several days and the crystals formed were recovered for a 62% yield of 1-ethoxycarbonylmethyl-3-methyl-benzimidazolium bromide. After crystallization from an ethyl acetate-methanol mixture, the product melted at 160°–161° C.

Analysis: $C_{12}H_{15}N_2O_2Br$; molecular weight=299. Calculated: %C 48.18, %H 5.05, %N 9.36, %Be 26.71. Found: %C 47.97, %H 5.14, %N 9.35, %Be 26.49.

I.R. Spectrum (KBr disc): 1239, 1745 cm$^{-1}$

STEP C: ethyl 5-methyl-4,5-dihydro-4-oxo-pyrrolo[1,2-a]quinoxaline-2-carboxylate 800 mg of dry triethylamine and then 1.13 g of ethyl propiolate were added to a suspension of 2.3 g of the product of Step B in 50 ml of dimethylformamide and the mixture was heated to 70° C. and then was allowed to stand at room temperature for 2 days. 300 ml of water and 200 ml of ethyl acetate were added thereto and the mixture was stirred. The mixture was decanted and the aqueous layer was extracted twice with 50 ml of ethyl acetate. The combined organic phases were washed with water, dried and filtered. The filtrate was evaporated to dryness and oil residue was triturated with ether. The mixture was filtered to obtain a 41% yield of ethyl 5-methyl-4,5-dihydro-4-oxo-pyrrolo[1,2-a]quinoxaline-2-carboxylate which melted at 197°–198° C. after crystallization from ethyl acetate.

Analysis: $C_{15}H_{14}N_2O_3$; molecular weight=270. Calculated: %C 66.66, %H 5.22, %N 10.36. Found: %C 66.62, %H 5.20, %N 10.31.

I.R. Spectrum (KBr disc): 1275, 1666, 1720 and 3140 cm$^{-1}$

EXAMPLE 2 ethyl 5-phenyl-4,5-dihydro-4-oxo-pyrrolo[1,2-a]quinoxaline-2-carboxylate

STEP A: 1-ethoxycarbonylmethyl-3-phenyl-benzimidazolium bromide

Using the procedure of Step B of Example 1, 1-phenylbenzimidazole [prepared from N-phenyl-o-phenylenediamine with 4HCl and formic acid] and ethyl bromoacetate were reacted to obtain a 56% of 1-ethoxycarbonylmethyl-3-phenyl-benzimidazolium bromide which after crystallization from a mixture of ethyl acetate and methanol melted at 180°–181° C.

Analysis: $C_{17}H_{17}N_2O_2Br$; molecular weight=361. Calculated: %C 56.52 %H 4.74 %N 7.75 %Br 22.12 Found: %C 56.30, %H 4.66, %N 7.77, %Br 22.14.

I.R. Spectrum (KBr disc): 1212, 1232, 1755 cm$^{-1}$

STEP B: ethyl 5-phenyl-4,5-dihydro-4-oxo-pyrrolo[1,2-a]quinoxaline-2-carboxylate Using the procedure of Step C of Example 1, the product of Step A was reacted to obtain a 35% yield of ethyl 5-phenyl-4,5-dihydro-4-oxo-pyrrolo[1,2-a]quinoxaline-2-carboxylate which melted at 256°–259° C. after crystallization from ether.

Analysis: $C_{20}H_{16}N_2O_3$: molecular weight=332. Calculated: %C 72.28, %H 4.85, %N 8.43. Found: %C 71.84, %H 4.86, %N 8.37.

I.R. Spectrum (KBr disc): 1280, 1677, 1711, 3135 cm$^{-1}$

EXAMPLE 3 ethyl 5-ethyl-4,5-dihydro-4-oxo-pyrrolo[1,2-a]quinoxaline-2-carboxylate

STEP A: 1-ethoxycarbonylmethyl-3-ethyl-benzimidazolium bromide

Using the procedure of Step B of Example 1, 1-ethyl benzimidazole [prepared by reacting benzimidazole with bromoethane] was reacted to obtain a 57% yield of 1-ethoxycarbonylmethyl-3-ethyl-benzimidazolium bromide which melted at 119°–121° C. after crystallization from an ether-methanol mixture.

Analysis: $C_{13}H_{17}N_2O_2Br.H_2O$ molecular weight=331. Calculated: %C 47.14, %H 5.78, %N 8.46, %Br 24.13. Found: %C 47.36, %H 5.57, %N 8.51, %Br 24.27.

I.R. Spectrum (KBr disc): 1225, 1749, 3450 cm$^{-1}$

STEP B: ethyl 5-ethyl-4,5-dihydro-4-oxo-pyrrolo[1,2-a]quinoxaline-2-carboxylate

Using the procedure of Step C of Example 1, the product of Step A was reacted to obtain a 50% yield of ethyl 5-ethyl-4,5-dihydro-4-oxo-pyrrolo[1,2-a]quinoxaline-2-carboxylate melting at 184°–186° C. after crystallization from ether.

Analysis: $C_{16}H_{16}N_2O_3$; molecular weight=284. Calculated: %C 67.59, %H 5.67, %N 9.85. Found: %C 67.47, %H 5.63, %N 9.85.

I.R. Spectrum (KBr disc): 1275, 1654, 1715, 3125 cm$^{-1}$

EXAMPLE 4 ethyl 5-n-propyl-4,5-dihydro-4-oxo-pyrrolo[1,2-a]quinoxaline-2-carboxylate

STEP A: 1-ethoxycarbonylmethyl-3-n-propyl-benzimidazolium bromide

Using the procedure of Step B of Example 1, 1-n-propyl-benzimidazole [prepared by reacting benzimidazole with iodopropane] was reacted to obtain a 76% yield of 1-ethoxycarbonylmethyl-3-n-propyl-benzimidazolium bromide which melted at 169°–170° C. after crystallization from an ethermethanol mixture.

Analysis: $C_{14}H_{19}N_2O_2Br \cdot H_2O$; molecular weight=345. Calculated: %C 48.71, %H 6.13, %N 8.11, %Br 23.15. Found: %C 48.95, %H 5.81, %N 8.26, %Br 23.56.

I.R. Spectrum (KBr disc): 1231, 1754, 3450 cm$^{-1}$

STEP B: ethyl 5-n-propyl-4,5-dihydro-4-oxo-pyrrolo[1,2-a]quinoxaline-2-carboxylate Using the procedure of Step C of Example 1, the product of Step A was reacted to obtain a 37% yield of ethyl 5-n-propyl-4,5-dihydro-4-oxo-pyrrolo[1,2-a]quinoxaline-2-carboxylate melting at 143°–144° C. after crystallization from ether.

Analysis: $C_{17}H_{18}N_2O_3$: molecular weight=298. Calculated: %C 68.44, %H 6.08, %N 9.39. Found: %C 68.26, %H 6.17, %N 9.38.

I.R. Spectrum (KBr disc): 1272, 1666, 1718, 3135 cm$^{-1}$

EXAMPLE 5 ethyl 5-n-butyl-4,5-dihydro-4-oxo-pyrrolo[1,2-a]quinoxaline-2-carboxylate

STEP A: 1-ethoxycarbonylmethyl-3-n-butyl-benzimidazolium bromide

Using the procedure of Step B of Example 1, 1-n-butyl-benzimidazole [prepared by reacting benzimidazole with bromobutane] was reacted to obtain a 49% yield of 1-ethoxycarbonylmethyl-3-n-butyl-benzimidazolium bromide which melted at 154°–156° C. after crystallization from an ethermethanol mixture.

Analysis: $C_{15}H_{21}N_2O_2Br$; molecular weight=341. Calculated: %C 52.80, %H 6.20, %N 8.21, %Br 23.42. Found: %C 52.61, %H 6.27, %N 8.17, %Br 23.49.

I.R. Spectrum (KBr disc): 1270, 1742 cm$^{-1}$

STEP B: ethyl 5-n-butyl-4,5-dihydro-4-oxo-pyrrolo[1,2-a]quinoxaline-2-carboxylate Using the procedure of Step C of Example 1, the product of Step A was reacted to obtain a 44% yield of ethyl 5-n-butyl-4,5-dihydro-4-oxo-pyrrolo[1,2-a]quinoxaline-2-carboxylate melting at 146°–148° C. after crystallization from ether.

Analysis: $C_{18}H_{20}N_2O_3$: molecular weight=312. Calculated: %C 69.21, %H 6.45, %N 8.97. Found: %C 69.22, %H 6.49, %N 8.97.

I.R. Spectrum (KBr disc): 1270, 1658, 1711, 3135 cm$^{-1}$

EXAMPLE 6 ethyl 5-n-pentyl-4,5-dihydro-4-oxo-pyrrolo[1,2-a]quinoxaline-2-carboxylate

STEP A: 1-ethoxycarbonylmethyl-3-n-pentyl-benzimidazolium bromide

Using the procedure of Step B of Example 1, 1-n-pentylbenzimidazol [prepared by reacting benzimidazole with bromopentane] was reacted to obtain a 42% yield of 1-ethoxycarbonylmethyl-3-n-pentyl-benzimidazolium bromide which melted at 116°–117° C. after crystallization from an ether-methanol mixture.

Analysis: $C_{16}H_{23}N_2O_2Br \cdot \frac{1}{2}H_2O$; molecular weight=364. Calculated: %C 52.56, %H 6.60, %N 7.65, %Br 21.82. Found: %C 52.58, %H 6.34 %N 7.63, %Br 22.13.

I.R. Spectrum (KBr disc): 1230, 1760, 3450 cm$^{-1}$

STEP B: ethyl 5-n-pentyl-4,5-dihydro-4-oxo-pyrrolo[1,2-a]quinoxaline-2-carboxylate Using the procedure of Step C of Example 1, the product of Step A was reacted to obtain a 43% yield of ethyl 5-n-pentyl-4,5-dihydro-4-oxo-pyrrolo[1,2-a]quinoxaline-2-carboxylate melting at 151°–152° C. after crystallization from ether.

Analysis: $C_{19}H_{22}N_2O_3$; molecular weight=326. Calculated: %C 69.92, %H 6.79, %N 8.58. Found: %C 69.92, %H 6.77, %N 8.58.

I.R. Spectrum (KBr disc): 1270, 1663, 1713, 3135 cm$^{-1}$

EXAMPLE 7 ethyl 5-isopropyl-4,5-dihydro-4-oxo-pyrrolo[1,2-a]quinoxaline-2-carboxylate

STEP A: 1-ethoxycarbonylmethyl-3-isopropyl-benzimidazolium bromide

Using the procedure of Step B of Example 1, 1-isopropyl benzimidazole [prepared by reacting benzimidazole with isopropylbromide] was reacted to obtain a 47% yield of 1-ethoxycarbonylmethyl-3-isopropyl-benzimidazolium bromide which melted at 110°–115° C. after crystallization from an ether-methanol mixture.

Analysis: $C_{14}H_{19}N_2O_2Br \cdot H_2O$; molecular weight=345. Calculated: %C 48.71, %H 6.13, %N 8.11, %Br 23.15. Found: %C 48.6, %H 6.12, %N 8.04, %Br 23.57.

I.R. Spectrum (KBr disc): 1241, 1743, 3450 cm$^{-1}$

STEP B: ethyl 5-isopropyl-4,5-dihydro-4-oxo-pyrrolo[1,2-a]quinoxaline-2-carboxylate Using the procedure of Step C of Example 1, the product of Step A was reacted to obtain a 22% yield of ethyl 5-isopropyl-4,5-dihydro-4-oxo-pyrrolo[1,2-a]quinoxaline-2-carboxylate melting at 169°–170° C. after crystallization from ether.

Analysis: $C_{17}H_{18}N_2O_3$: molecular weight=298. Calculated: %C 68.44, %H 6.08, %N 9.39. Found: %C 68.41 %H 6.04, %N 9.38.

I.R. Spectrum (KBr disc): 1266, 1659, 1714, 3135 cm$^{-1}$

EXAMPLE 8 ethyl 5-allyl-4,5-dihydro-4-oxo-pyrrolo[1,2-a]quinoxaline-2-carboxylate

STEP A: 1-ethoxycarbonylmethyl-3-allyl-benzimidazolium bromide

Using the procedure of Step B of Example 1, 1-allyl benzimidazole [prepared by reacting benzimidazole with allyl bromide] was reacted to obtain a 22% yield of 1-ethoxycarbonylmethyl-3-allyl-benzimidazolium bromide which melted at 166°–168° C. after crystallization from an ether-methanol mixture.

Analysis: $C_{14}H_{17}N_2O_2Br$; molecular weight=325. Calculated: %C 51.71, %H 5.27, %N 8.61, %Br 24.57. Found: %C 51.50, %H 5.21, %N 8.68, %Br 24.71.

I.R. Spectrum (KBr disc): 1226, 1753 cm$^{-1}$

STEP B: ethyl 5-allyl-4,5-dihydro-4-oxo-pyrrolo[1,2-a]quinoxaline-2-carboxylate Using the procedure of Step C of Example 1, the product of Step A was reacted to obtain a 35% yield of ethyl 5-allyl-4,5-dihydro-4-oxo-pyrrolo[1,2-a]quinoxaline-2-carboxylate melting at 177°–178° C. after crystallization from ether.

Analysis: $C_{17}H_{16}N_2O_3$: molecular weight=296. Calculated: %C 68.91, %H 5.44, %N 9.45. Found: %C 68.88, %H 5.41, %N 9.46.

I.R. Spectrum (KBr disc): 1274, 1646, 1663, 3125, 1717 cm$^{-1}$

EXAMPLE 9 ethyl 5-cyclopentyl-4,5-dihydro-4-oxo-pyrrolo[1,2-a]quinoxaline-2-carboxylate

STEP A: 1-ethoxycarbonylmethyl-3-cyclopentyl-benzimidazolium bromide

Using the procedure of Step B of Example 1, 1-cyclopentyl benzimidazole [prepared by reacting benzimidazole with cyclopentyl bromide] was reacted to obtain a 31.5% yield of 1-ethoxycarbonylmethyl-3-cyclopentyl-benzimidazolium bromide which melted at 119°–121° C. after crystallization from an ether-methanol mixture.

Analysis: $C_{16}H_{21}N_2O_2Br \cdot H_2O$; molecular weight=371. Calculated %C 51.76, %H 6.24, %N 7.54, %Br 21.52. Found: %C 51.60, %H 6.06, %N 7.70, 21.88.

I.R. Spectrum (KBr disc): 1222, 1751, 3450 cm$^{-1}$

STEP B: ethyl 5-cyclopentyl-4,5-dihydro-4-oxo-pyrrolo[1,2-a]quinoxaline-2-carboxylate Using the procedure of Step C of Example 1, the product of Step A was reacted to obtain a 20% yield of ethyl 5-cyclopentyl-4,5-dihydro-4-oxo-pyrrolo[1,2-a]quinoxaline-2-carboxylate melting at 183°–185° C. after crystallization from ether.

Analysis: $C_{19}H_{20}N_2O_3$: molecular weight=324. Calculated: %C 70.35, %H 6.21, %N 8.64. Found: %C 70.20, %H 6.33, %N 8.68.

I.R. Spectrum (KBr disc): 1269, 1658, 1712, 3135 cm$^{-1}$

EXAMPLE 10 ethyl 5-n-butyl-8-chloro-4,5-dihydro-4-oxo-pyrrolo[1,2-a]quinoxaline-2-carboxylate

STEP A: 1-ethoxycarbonylmethyl-3-n-butyl-6-chloro-benzimidazolium bromide

Using the procedure of Step B of Example 1, 1-n-butyl-6-chloro-benzimidazole [prepared from the corresponding o-phenylenediamine] was reacted to obtain a crude oil of 1-ethoxy carbonylmethyl-3-n-butyl-6-chloro-benzimidazolium bromide which was used as is for the next step.

STEP B: ethyl 5-n-butyl-8-chloro-4,5-dihydro-4-oxo-pyrrolo[1,2-a]quinoxaline-2-carboxylate Using the procedure of Step C of Example 1, the product of Step A was reacted to obtain a 30% yield of ethyl 5-n-butyl-8-chloro-4,5-dihydro-4-oxo-pyrrolo[1,2-a]quinoxaline-2-carboxylate melting at 172°–174° C. after crystallization from ether.

Analysis: $C_{18}H_{19}N_2O_3Cl$; molecular weight=346.5. Calculated: %C 62.34, %H 5.52, %N 8.08, %Cl 10.22. Found: %C 62.09, %H 5.41, %N 8.07, %Cl 10.34.

I.R. Spectrum (KBr disc): 1278, 1683, 1720, 3120 cm$^{-1}$

EXAMPLE 11 ethyl 5-n-butyl-7,8-dichlor-4,5-dihydro-4-oxo-pyrrolo[1,2-a]quinoxaline-2-carboxylate

STEP A: 1-ethoxycarbonylmethyl-3-n-butyl-5,6-dichlorobenzimidazolium bromide Using the procedure of Step B of Example 1, 1-n-butyl-5,6-dichloro-benzimidazole [prepared from the corresponding o-phenylenediamine] was reacted to obtain a crude oil of 1-ethoxycarbonylmethyl-3-n-butyl-5,6-dichloro-benzimidazolium bromide which was used as is for the next step.

STEP B: ethyl 5-n-butyl-7,8-dichloro-4,5-dihydro-4-oxo-pyrrolo[1,2-a]quinoxaline-2-carboxylate Using the procedure of Step C of Example 1, the product of Step A was reacted to obtain 13% yield of ethyl 5-n-butyl-7,8-dichloro-4,5-dihydro-4-oxo-pyrrolo[1,2-a]quinoxaline-2-carboxylate melting at 179°–180° C. after crystallization from an ether-ethylacetate mixture.

Analysis: $C_{18}H_{18}N_2O_3Cl_2$; molecular weight=381. Calculated: %C 56.71, %H 4.76, %N 7.35, %Cl 18.60. Found: %C 56.67, %H 4.69, %N 7.42, %Cl 18.49.

I.R. Spectrum (KBr disc): 1280, 1690, 1719, 3120 $cm^{-1}$

EXAMPLE 12

5-methyl-4,5-dihydro-4-oxo-pyrrolo[1,2-a]quinoxaline-2-carboxylic acid

A solution of 0.9 g of sodium hydroxide in 50 ml of water was added to a suspension of 1.66 g of ethyl 5-methyl-4,5-dihydro-4-oxo-pyrrolo[1,2-a]quinoxaline-2-carboxylate in 30 ml of hot ethanol and the mixture was warmed on a water bath for one hour after which thin layer chromatography showed no ester present. The resulting solution was filtered hot and the filtrate was acidified to a pH of 1–2 with concentrated hydrochloric acid. The mixture was cooled and filtered and the recovered product was rinsed with water and dried over $P_2O_5$ under vacuum to obtain 1.40 g (95% yield) of 5-methyl-4,5-dihydro-4-oxo-pyrrolo[1,2-a]quinoxaline-2-carboxylic acid melting at 330°–333° C.

Analysis: $C_{13}H_{10}N_2O_3$; molecular weight=242. Calculated: %C 64.46, %H 4.16, %N 11.56. Found: %C 64.18, %H 4.02, %N 11.54.

I.R. Spectrum (KBr disc): 1280, 1666, 1700, 3165 $cm^{-1}$

EXAMPLE 13

5-phenyl-4,5-dihydro-4-oxo-pyrrolo[1,2-a]quinoxaline-2-carboxylic acid

Using the procedure of Example 12, ethyl 5-phenyl-4,5-dihydro-4-oxo-pyrrolo[1,2-a]quinoxaline-2-carboxylate was reacted to obtain a 65% yield of 5-phenyl-4,5-dihydro-4-oxo-pyrrolo[1,2-a]quinoxaline-2-carboxylic acid melting at 304°–306° C. after crystallization from ethanol.

Analysis $C_{18}H_{12}N_2O_3$; molecular weight=304. Calculated: %C 71.05, %H 3.97, %N 9.21. Found: %C 70.89, %H 4.10, %N 9.28.

I.R. Spectrum (KBr disc): 1260, 1666, 1700, 3165 $cm^{-1}$

EXAMPLE 14

5-ethyl-4,5-dihydro-4-oxo-pyrrolo[1,2-a]quinoxaline-2-carboxylic acid

Using the procedure of Example 12, ethyl 5-ethyl-4,5-dihydro-4-oxo-pyrrolo[1,2-a]quinoxaline-2-carboxylate was reacted to obtain a 91% yield of 5-ethyl-4,5-dihydro-4-oxo-pyrrolo[1,2-a]quinoxaline-2-carboxylic acid melting at 314°–316° C. after crystallization from an ethanol-water mixture.

Analysis: $C_{14}H_{12}N_2O_3$; molecular weight=256. Calculated %C 65.62, %H 4.72, %N 10.93. Found: %C 65.39, %H 4.79, %N 10.88.

I.R. Spectrum (KBr disc): 1282, 1656, 1698, 3140 $cm^{-1}$

EXAMPLE 15

5-n-propyl-4,5-dihydro-4-oxo-pyrrolo[1,2-a]quinoxaline-2-carboxylic acid

Using the procedure of Example 12, ethyl 5-n-propyl-4,5-dihydro-4-oxo-pyrrolo[1,2-a]quinoxaline-2-carboxylate was reacted to obtain a 96% yield of 5-n-propyl-4,5-dihydro-4-oxo-pyrrolo[1,2-a]quinoxaline-2-carboxylic acid melting at 260°–262° C. after crystallization from an ethanol-water mixture.

Analysis: $C_{15}H_{14}N_2O_3$; molecular weight=270. Calculated: %C 66.66, %H 5.22, %N 10.36. Found: %C 66.57, %H 5.23, %N 10.38.

I.R. Spectrum (KBr disc): 1267, 1595, 1615, 1700, 3135 $cm^{-1}$

EXAMPLE 16

5-n-butyl-4,5-dihydro-4-oxo-pyrrolo[1,2-a]quinoxaline-2-carboxylic acid

Using the procedure of Example 12, ethyl 5-n-butyl-4,5-dihydro-4-oxo-pyrrolo-[1,2-a]quinoxaline-2-carboxylate was reacted to obtain a 89% yield of 5-n-butyl-4,5-dihydro-4-oxo-pyrrolo[1,2-a]quinoxaline-2-carboxylic acid melting at 212°–214° C. after crystallization from an ethanol-water mixture.

Analysis: $C_{16}H_{16}N_2O_3$: molecular weight=284. Calculated: %C 67.59, %H 5.67, %N 9.85. Found: %C 67.22, %H 5.72, %N 9.77.

I.R. Spectrum (KBr disc): 1270, 1590, 1615, 1715, 3140 $cm^{-1}$

EXAMPLE 17

5-n-pentyl-4,5-dihydro-4-oxo-pyrrolo[1,2-a]quinoxaline-2-carboxylic acid

Using the procedure of Example 12, ethyl 5-n-pentyl-4,5-dihydro-4-oxo-pyrrolo[1,2-a]quinoxaline-2-carboxylate was reacted to obtain a 95% yield of 5-n-pentyl-4,5-dihydro-4-oxo-pyrrolo[1,2-a]quinoxaline-2-carboxylic acid melting at 184°–186° C. after crystallization from a methanol-water mixture.

Analysis: $C_{17}H_{18}N_2O_3$: molecular weight=298. Calculated: %C 68.44, %H 6.08, %N 9.39. Found: %C 68.38, %H 6.10, %N 9.42.

I.R. Spectrum (KBr disc): 1268, 1590, 1617, 1715, 3125 $cm^{-1}$

EXAMPLE 18

5-isopropyl-4,5-dihydro-4-oxo-pyrrolo[1,2-a]quinoxaline-2-carboxylic acid

Using the procedure of Example 12, ethyl 5-isopropyl-4,5-dihydro-4-oxo-pyrrolo[1,2-a]quinoxaline-2-carboxylate was reacted to obtain a 94% yield of 5-isopropyl-4,5-dihydro-4-oxo-pyrrolo[1,2-a]quinoxaline-2-carboxylic acid melting at 238°–240° C. after crystallization from an ethanol-water mixture.

Analysis: $C_{15}H_{14}N_2O_3 \cdot \frac{1}{2}H_2O$; molecular weight=279. Calculated: %C 64.51, %H 5.41, %N 10.03. Found: %C 64.84, %H 5.56, %N 10.08.

I.R. Spectrum (KBr disc): 1255, 1630, 1696, 3135 $cm^{-1}$

EXAMPLE 19

5-allyl-4,5-dihydro-4-oxo-pyrrolo[1,2-a]quinoxaline-2-carboxylic acid

Using the procedure of Example 12, ethyl 5-allyl-4,5-dihydro-4-oxo-pyrrolo[1,2-a]quinoxaline-2-carboxylate was reacted to obtain a 96% yield of 5-allyl-4,5-dihydro-4-oxo-pyrrolo[1,2-a]quinoxaline-2-carboxylic acid melting at 306°–308° C. after crystallization from an ethanol-water mixture.

Analysis: $C_{15}H_{12}N_2O_3$: molecular weight=268. Calculated: %C 67.16, %H 4.51, %N 10.44. Found: %C 67.13, %H 4.51, %N 10.42.

I.R. Spectrum (KBr disc): 1280, 1650, 1700, 3130 $cm^{-1}$

EXAMPLE 20

5-cyclopentyl-4,5-dihydro-4-oxo-pyrrolo[1,2-a]quinoxaline-2-carboxylic acid

Using the procedure of Example 12, ethyl 5-cyclopentyl-4,5-dihydro-4-oxo-pyrrolo[1,2-a]quinoxaline-2-carboxylate was reacted to obtain a 95% yield of 5-cyclopentyl-4,5-dihydro-4-oxo-pyrrolo[1,2-a]quinoxaline-2-carboxylic acid melting at 215°–216° C. after crystallization from an ethanol-water mixture.

Analysis: $C_{17}H_{16}N_2O_3 \cdot \frac{1}{2}H_2O$; molecular weight=305. Calculated: %C 66.89, %H 5.62, %N 9.18. Found: %C 67.05, %H 5.67, %N 9.33.

I.S. Spectrum (KBr disc): 1280, 1650, 1685, 3130 $cm^{-1}$

EXAMPLE 21

5-n-butyl-8-chloro-4,5-dihydro-4-oxo-pyrrolo[1,2-a]quinoxaline-2-carboxylic acid Using the procedure of Example 12, ethyl 5-n-butyl-8-chloro-4,5-dihydro-4-oxo-pyrrolo[1,2-a]quinoxaline-2-carboxylate was reacted to obtain a 93% yield of 5-n-butyl-8-chloro-4,5-dihydro-4-oxo-pyrrolo[1,2-a]quinoxaline-2-carboxylic acid melting at 275°–276° C. after crystallization from ethanol.

Analysis: $C_{16}H_{15}N_2O_3Cl$; molecular weight=318.5. Calculated: %C 60.29, %H 4.74, %N 8.79, %Cl 11.12. Found: %C 60.24, %H 4.73, %N 8.83, %Cl 11.19.

I.R. Spectrum (KBr disc): 1290, 1645, 1685, 3140 $cm^{-1}$

EXAMPLE 22

5-n-butyl-7,8-dichloro-4,5-dihydro-4-oxo-pyrrolo[1,2-a]quinoxaline-2-carboxylic acid Using the procedure of Example 12, ethyl 5-n-butyl-7,8-dichloro-4,5-dihydro-4-oxo-pyrrolo[1,2-a]quinoxaline-2-carboxylate was reacted to obtain a 92% yield of 5-n-butyl-7,8-dichloro-4,5-dihydro-4-oxo-pyrrolo[1,2-a]quinoxaline-2-carboxylic acid melting at 281°–283° C. after crystallization from an ethanol-water mixture.

Analysis: $C_{16}H_{14}N_2O_3Cl_2$; molecular weight=353. Calculated: %C 54.41, %H 3.99, %N 7.93, %Cl 20.08. Found: %C 54.40, %H 3.98, %N 7.93, %Cl 19.93.

I.R. Spectrum (KBr disc): 1264, 1639, 1716, 3180 $cm^{-1}$

EXAMPLE 23

5-n-butyl-7 and 8-nitro-4,5-dihydro-4-oxo-pyrrolo[1,2-a]quinoxaline-2-carboxylic acid

STEP A: 5(6)-nitrobenzimidazole 15 ml of formic acid were added to a suspension of 15.3 g of 4-nitro-1,2-phenylenediamine in 150 ml of 10% hydrochloric acid and the mixture was stirred on a water bath at 80° C. for 3 hours and was cooled. The mixture was made alkaline with concentrated ammonium hydroxide solution and the mixture was filtered. The yellowish needles were washed with water and dried over $P_2O_5$ under reduced pressure to obtain 14.3 g (89% yield) of 5(6)-nitro-benzimidazole melting at 209°–211° C.

I.R. Spectrum: 739, 1304, 1349, 1470 and 1521 $cm^{-1}$

STEP B: ethyl 5-n-butyl-7(and 8-isomer mixture)-nitro-4,5-dihydro-4-oxo-pyrrolo[1,2-a]quinoxaline-2-carboxylate A mixture of 14.0 g of the product of Step A, 18.0 g of 1-bromo-butane, 5.6 g of potassium hydroxide, 100 ml of water and 50 ml of ethanol was refluxed for 6 hours and 100 ml of water were added to the mixture which was then cooled. The mixture was extracted three times with 100 ml of chloroform and the combined extracts were dried and filtered. The filtrate was evaporated to dryness and the oily residue was chromatographed over neutral alumina. Elution with chloroform yielded a crude oil mixture of 1-n-butyl-5-nitrobenzimidazole and its 6-nitro isomer (one TLC Spot) which was used as is.

16.6 g of the said oil was dissolved in 100 ml of benzene and 15 g of ethyl bromoacetate were added thereto. The mixture was refluxed for 5 hours during which an oil formed and thin layer chromatography of the solution showed little starting material therein. The oil was separated by decanting and was washed once with ether to obtain 30 g of raw product.

The crude product was dissolved in 200 ml of dimethylformamide and 9 g of triethylamine and 9 g of ethyl propiolate were added thereto. The mixture was stirred overnight at room temperature and was treated with ethyl acetate and water as in Example 1. The ethyl acetate phase was dried and filtered and the filtrate was evaporated to dryness. The oil residue was triturated with ether and was filtered. The yellow needles were dried over $P_2O_5$ under vacuum to obtain 3.1 g of a mixture of ethyl 5-n-butyl-7 and 8-nitro-4,5-dihydro-4-oxo-pyrrolo[1,2-a]quinoxaline-2-carboxylate melting at 184°–186° C.

I.R. Spectrum: 1270, 1347, 1679, 1711, 1731 and 3135 $cm^{-1}$

NMR Spectrum was consistent with about a 1:2 mixture of the 7- and 8-nitro isomers.

STEP C: 5-n-buty-7-(and 8-)-nitro-4,5-dihydro-4-oxo-pyrrolo[1,2-a]quinoxaline-2-carboxylic acid 450 mg of sodium hydroxide were added to a suspension of 1.05 g of the product of Step B in 50 ml of water and 30 ml of ethanol and the mixture was heated at 80° C. for one hour after which thin layer chromatography showed no starting material present. The solution was filtered hot and was acidified with concentrated hydrochloric acid to a pH of 1 to 2. The mixture was filtered and the yellow crystals were washed with water and dried over $P_2O_5$ under vacuum to obtain 900 mg (93% yield) of 5-n-butyl-7-(and 8)-nitro-4,5-dihydro-4-oxo-pyrrolo[1,2-a]quinoxaline-2-carboxylic acid melting at 236°–256° C. (with decomposition).

I.R. Spectrum: 1217, 1250, 1300, 1340, 1534, 1611, 1640–1690, 1720, 2100–3600, 3140 $cm^{-1}$ NMR Spectrum consistent with about a 1:2 mixture of 7- and 8-nitro isomers.

Analysis: $C_{16}H_{15}N_3O_5 \cdot \frac{1}{2}H_2O$. Calculated: %C 56.80, %H 4.77, %N 12.42. Found: %C 56.77, %H 4.75, %N 12.42.

Chromatography over silica and elution with a methanol-ethyl acetate mixture yielded the 8-isomer melting at 280°–282° C. with decomposition.

I.R. Spectrum: 1249, 1340, 1371, 1532, 1611, 1669, 1711, 2300–3600, 3140 $cm^{-1}$ Calculated: %C 58.36, %H 4.59, %N 12.76. Found: %C 58.32, %H 4.79, %N 12.46.

NMR Spectrum (DMSO-D$_6$): 1.05 (d,l, J=2Hz, H$_9$); 1.17 (d,l, J=1Hz, H$_1$); 1.90 (dd,l, J=2, 9Hz, H$_7$); 2.43 (d,l, J=9Hz, H$_6$); 2.82 (d, l, J=1Hz, H$_3$); 5.7–6.2 and 8.2–9.3 (m, ~9H, >N—CH$_2$—CH$_2$—CH$_2$—CH$_3$ group). τ.

EXAMPLE 24

8-chloro-5-ethyl-4,5-dihydro-4-oxo-pyrrolo[1,2-a]quinoxaline-2-carboxylic acid

STEP A: N-ethyl-4-chloro-2-nitro-aniline

A mixture of 26 g of 2,5-dichloro-nitrobenzene, 400 ml of ethanol and 25 ml of ethylamine was refluxed for 24 hours while adding 5 ml of ethylamine at 6 hour intervals and the mixture was cooled and filtered. The orange needles were washed with a small amount of an ethanol-ether mixture and dried over P$_2$O$_5$ under vacuum to obtain 24.4 g (89% yield) of N-ethyl-4-chloro-2-nitro-aniline melting at 90°–91° C.

Analysis: C$_8$H$_9$N$_2$O$_2$Cl. Calculated: %C 47.90, %H 4.52, %N 13.96, %Cl 17.67. Found: %C 47.91, %H 4.56, %N 14.07, %Cl 17.65.

I.R. Spectrum: 800, 1160, 1267, 1407, 1510, 1571, 1626 and 3370 cm$^{-1}$

STEP B: 6-chloro-3-ethyl-1-ethoxycarbonylmethyl-benzimidiazolium bromide

A mixture of 16.7 g of the product of Step A in 250 ml of ethanol and 0.8 g of 5% platinized carbon was hydrogenated until thin layer chromatography showed the reaction to be complete and the mixture was filtered through celite. The ethanol was evaporated and the crude product was treated with 1 ml of formic acid per g of product in 200 ml of 4 N hydrochloric acid. The mixture was refluxed for 2 hours and was cooled and extracted 3 times with 75 ml of chloroform. The combined extracts were evaporated to dryness and the oil residue was chromatographed over neutral grade alumina. Elution with chloroform yielded 1-ethyl-5-chloro-benzimidazole as a brownish oil which was used as is.

14.2 g of the crude oil were dissolved in 400 ml of ether and 10 g of ethyl bromoacetate were added thereto. The mixture stood at room temperature for 3 days and was then filtered. The recovered precipitate was rinsed with ether and crystallized from a methanol-ether mixture to obtain 22.45 g (78% yield) of 6-chloro-3-ethyl-1-ethoxycarbonylmethyl-benzimidazolium bromide melting at 186°–190° C.

Analysis: C$_{13}$H$_{16}$N$_2$O$_2$ClBr. Calculated: %C 44.91, %H 4.64, %N 8.06, %Cl 10.20, %Br 22.99. Found: %C 44.88, %H 4.58, %N 8.06, %Cl 10.00, %Br 22.80.

I.R. Spectrum: 802, 1160, 1218, 1233, 1378, 1561, 1746 cm$^{-1}$

STEP C: ethyl 8-chloro-5-ethyl-4,5-dihydro-4-oxo-pyrrolo[1,2-a]quinoxaline-2-carboxylate A solution of 8.0 g of the product of Step B, 100 ml of dimethylformamide, 2.5 g of anhydrous triethylamine and 2.8 g of ethyl propiolate stood for 2 days at room temperature and then was worked up as in Example 1 with a water-ethyl acetate mixture. The ethyl acetate phase was washed with water, dried and filtered and the filtrate was evaporated to dryness. The oil residue was triturated with ether and was filtered. The buff colored needles were dried over P$_2$O$_5$ under vacuum to obtain 1.3 g (18% yield) of ethyl 8-chloro-5-ethyl-4,5-dihydro-4-oxo-pyrrolo[1,2-a]quinoxaline-2-carboxylate melting at 230°–232° C.

Analysis: C$_{16}$H$_{15}$N$_2$O$_3$Cl. Calculated: %C 60.29, %H 4.74, %N 8.79, %Cl 11.12. Found: %C 60.34, %H 4.79, %N 8.84, %Cl 11.15.

I.R. Spectrum: 756, 1278, 1290, 1369, 1524, 1659, 1722, 3130 cm$^{-1}$

STEP D: 8-chloro-5-ethyl-4,5-dihydro-4-oxo-pyrrolo[1,2-a]quinoxaline-2-carboxylic acid 0.95 g of the product of Step C was suspended in 20 ml of hot ethanol and a solution of 0.4 g of sodium hydroxide in 50 ml of water was added thereto. The mixture was warmed on a water bath for one hour after which thin layer chromatography showed no starting material and the solution was filtered hot. The filtrate was acidified to a pH of 1–2 with concentrated hydrochloric acid and was filtered. The recovered product was rinsed with water and dried over P$_2$O$_5$ under vacuum to obtain 0.70 g (81% yield) of 8-chloro-5-ethyl-4,5-dihydro-4-oxo-pyrrolo[1,2-a]quinoxaline-2-carboxylic acid melting at 322°–326° C.

Analysis: C$_{14}$H$_{11}$N$_2$O$_3$Cl Calculated: %C 57.84, %H 3.81, %N 9.64, %Cl 12.19. Found: %C 57.93, %H 3.92, %N 9.68.

I.R. Spectrum: 761, 1279(b), 1421, 1661, 1696, 2100–3200, 3120 cm$^{-1}$

EXAMPLE 25 sodium 5-methyl-4,5-dihydro-4-oxo-pyrrolo[1,2-a]quinoxaline-2-carboxylate

An aqueous solution of sodium hydroxide was added to a solution of 5-methyl-4,5-dihydro-4-oxo-pyrrolo[1,2-a]quinoxaline-2-carboxylic acid in ethanol and sodium 5-methyl-4,5-dihydro-4-oxo-pyrrolo[1,2-a]quinoxaline-2-carboxylate melting at 358°–360° C. was recovered from the mixture.

Analysis: C$_{13}$H$_9$N$_2$O$_3$Na.2H$_2$O. Calculated: %C 52.00, %H 4.36, %N 9.33. Found: %C 51.78, %H 4.31, %N 9.32.

EXAMPLE 26

Tablets were prepared containing 2 mg of 5-ethyl-4,5-dihydro-4-oxo-pyrrolo[1,2-a]quinoxaline-2-carboxylic acid or 5-n-propyl-4,5-dihydro-4-oxo-pyrrolo[1,2-a]quinoxaline-2-carboxylic acid or 5-n-butyl-4,5-dihydro-4-oxo-pyrrolo [1,2-a]quinoxaline-2-carboxylic acid and sufficient excipient of lactose, starch, talc and magnesium stearate to obtain a final tablet of 100 mg.

PHARMACOLOGICAL STUDY

Passive cutaneous anaphylaxis (PCA) in rats

Cutaneous anaphylaxis can be induced in rats by intradermal (ID) sensitization with antiserum followed three days later by systemic challenge with antigen. Evans blue dye injected with the antigen is used as a marker to assess the severity of the local response. Antiallergic drugs inhibit this reaction. This method has been described by OVARY (1962) "Passive Cutaneous Anaphylaxis in Allergology" Page 358–367 Ed. Brown: Pergamon Press: —male rats weighing 180–220 grams are used in groups of seven.

Preparation of Antigen for Sensitization (Alum precipitated ovalbumen)

1. Wash 120 grams of Al(OH)₃ in 140 ml of saline (use of a macerater facilitates mixing).
2. Centrifuge at 3,000 r.p.m. for about 10 minutes.
3. Resuspend the precipiate with 300 ml of albumen egg powder (1.3 mg/ml) in saline and allow to stand for 30 minutes.
4. Centrifuge at 3,000 r.p.m. for 10 minutes.
5. Weigh the wet precipitate and to each gram weight add 1 ml of saline. Store in refrigerator (Quantity sufficient for 60 rats for a 3 day sensitization program).

Preparation of Antiserum (anti-ovalbumen)

1 ml of the alum precipitated ovalbumen was injected subcutaneously into rats weighing 180–200 grams on days 0,2,4. The rats were bled on day 14 either by cardiac puncture or via the dorsal abdominal aorta. Equal quantities of serum from each animal were pooled and thoroughly mixed and 2 ml aliquots were stored at −20° C. in plastic tubes.

Serum Dilution for PCA

The antiserum for sensitization was diluted so that an ID injection of 0.1 ml into control animals would give an average score of a single spot of between 2.0–3.5 using a 5 point scoring system (0,1,2,3,4).

Method (A) SENSITIZATION: The rats were anaesthetized with Nembutal (40–60 mg/kg i.p.) and were then sensitized by four ID injections (0.1 ml each) on their shaved backs. The animals were then left for a period of three days to develop sensitization.

(B) CHALLENGE: The sensitized rats were dosed orally or intraveneously with the drug immediately prior to intravenous challege via the superficial penile vein with 1 ml of an antigen/Evans blue mixture (1 mg albumen egg powder in 0.5 ml saline plus 0.5 ml of 1% Evans blue). The injections were speeded up by using an automatic 1 ml self-filling glass syringe. The "challenged" rats were killed after 30 minutes, usually pithed) and their skin on the dorsal surface was removed. The degree and area of blueing, proportional to the anaphylactic reaction was assessed on a five point scoring system.

Calculations

1. Total scores for sites 1,2,3 and 4=X
2. Mean value of X for each group=$\bar{X}$
3. 
   $\bar{X}$ t=$\bar{X}$ for test group
   $\bar{X}$ c=$\bar{X}$ for control group
4.

$$\% \text{ inhibition} = \frac{\bar{X}c - \bar{X}t}{\bar{X}c} \times \frac{100}{1}$$

5. ED₅₀=dose of drug giving 50% inhibition.

ED₅₀ values for the compound tested in the passive cutaneous anaphylaxis screen (in rats) are as follows:

| COMPOUND OF EXAMPLE | ED 50 mg/kg i.v. | ED 50 mg/kg p.o. |
|---|---|---|
| 1 | — | 7.0 |
| 5 | — | 4.1 |
| 12 | 0.089 | 0.54 |
| 13 | 1.57 | 19 |
| 14 | 0.026 | 0.035 |
| 15 | 0.019 | 0.032 |
| 16 | 0.019 | 0.058 |
| 17 | 0.087 | 0.31 |
| 18 | 0.85 | — |
| 19 | 0.035 | 0.28 |
| 20 | 0.37 | — |
| 21 | 0.019 | 0.114 |
| 22 | 0.014 | 0.117 |
| 23(c) | 0.025 | 0.26 |
| 24(d) | 0.035 | 0.29 |

The data of Table I shows that the tested compounds possess antiallergic activity.

Various modifications of the compounds and processes of the invention may be made without departing from the spirit or scope thereof and it should be understood that the invention is not intended to be limited to the specific embodiments.

We claim:
1. A compound selected from the group consisting of a compound of the formula

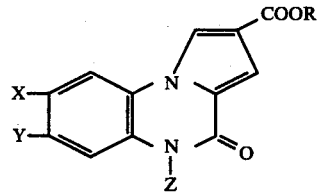

wherein X and Y are individually selected from the group consisting of hydrogen, halogen, alkyl and alkoxy of 1 to 5 carbon atoms and —NO₂, Z is selected from the group consisting of alkyl of 1 to 8 carbon atoms, cycloalkyl of 3 to 8 carbon atoms, alkenyl of 2 to 6 carbon atoms and phenyl and R is selected from the group consisting of hydrogen, alkyl of 1 to 5 carbon atoms,

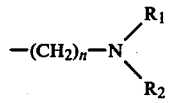

and non-toxic, pharmaceutically acceptable cations, n is an integer from 1 to 6 and R₁ and R₂ are individually alkyl of 1 to 5 carbon atoms and the non-toxic, pharmaceutically acceptable acid addition salts thereof.

2. A compound of claim 1 wherein X and Y are hydrogen, R is ethyl and Z is methyl or ethyl.

3. A compound of claim 1 wherein X and Y are individually selected from the group consisting of hydrogen, chlorine, bromine, methyl, methoxy and nitro.

4. A compound of claim 1 wherein Z is selected from group consisting of alkyl of 1 to 8 carbon atoms, cyclopentyl, allyl and phenyl and R is selected from the group consisting of hydrogen and alkyl of 1 to 5 carbon atoms.

5. A compound of claim 1 wherein R is hydrogen.

6. A compound of claim 1 wherein X and Y are individually selected from the group consisting of hydrogen, chlorine and nitro and Z is selected from the group consisting of alkyl of 1 to 5 carbon atoms, cyclopentyl, allyl and phenyl.

7. A compound of claim 6 wherein Z is straight chain alkyl of 1 to 5 carbon atoms.

8. A compound of claim 1 selected from the group consisting of 5-methyl-4,5-dihydro-4-oxo-pyrrolo[1,2-a]quinoxaline-2-carboxylic acid and its non-toxic, pharmaceutically acceptable salts and acid addition salts.

9. A compound of claim 1 selected from the group consisting of 5-ethyl-4,5-dihydro-4-oxo-pyrrolo[1,2-a]quinoxaline-2-carboxylic acid and its non-toxic, pharmaceutically acceptable salts and acid addition salts.

10. A compound of claim 1 selected from the group consisting of 5-n-propyl-4,5-dihydro-4-oxo-pyrrolo[1,2-a]quinoxaline-2-carboxylic acid and its non-toxic, pharmaceutically acceptable salts and acid addition salts.

11. A compound of claim 1 selected from the group consisting of 5-n-butyl-4,5-dihydro-4-oxo-pyrrolo[1,2-a]quinoxaline-2-carboxylic acid and its non-toxic, pharmaceutically acceptable salts and acid addition salts.

12. A compound of claim 1 selected from the group consisting of 8-chloro-5-n-butyl-4,5-dihydro-4-oxo-pyrrolo[1,2-a]quinoxaline-2-carboxylic acid and its non-toxic, pharmaceutically acceptable salts and acid addition salts.

13. A compound of claim 1 selected from the group consisting of 7,8-dichloro-5-n-butyl-4,5-dihydro-4-oxo-pyrrolo[1,2-a]quinoxaline-2-carboxylic acid and its non-toxic, pharmaceutically acceptable salts and acid addition salts.

14. An antiallergic composition comprising an antiallergically effective amount of at least one compound of claim 1 and an inert pharmaceutical carrier.

15. A composition of claim 14 wherein X and Y are hydrogen, R is ethyl and Z is methyl or ethyl.

16. A composition of claim 14 wherein X and Y are individually selected from the group consisting of hydrogen, chlorine, bromine, methyl, methoxy and nitro.

17. A composition of claim 14 wherein Z is selected from the group consisting of alkyl of 1 to 8 carbon atoms, cyclopentyl, allyl and phenyl and R is selected from the group consisting of hydrogen and alkyl of 1 to 5 carbon atoms.

18. A composition of claim 14 wherein R is hydrogen.

19. A composition of claim 14 wherein X and Y are individually selected from the group consisting of hydrogen, chlorine and nitro and Z is selected from the group consisting of alkyl of 1 to 5 carbon atoms, cyclopentyl, allyl and phenyl.

20. A composition of claim 14 wherein Z is straight chain alkyl of 1 to 5 carbon atoms.

21. A method of treating allergies in warm-blooded animals comprising administering to warm-blooded animals an antiallergically effective amount of a composition of claim 14.

22. A method of claim 21 wherein X and Y are hydrogen, R is ethyl and Z is methyl or ethyl.

23. A method of claim 21 wherein X and Y are individually selected from the group consisting of hydrogen, chlorine, bromine, methyl, methoxy and nitro.

24. A method of claim 21 wherein Z is selected from the group consisting of alkyl of 1 to 8 carbon atoms, cyclopentyl, allyl and phenyl and R is selected from the group consisting of hydrogen and alkyl of 1 to 5 carbon atoms.

25. A method of claim 21 wherein R is hydrogen.

26. A method of claim 21 wherein X and Y are individually selected from the group consisting of hydrogen, chlorine and nitro and Z is selected from the group consisting of alkyl of 1 to 5 carbon atoms, cyclopentyl, allyl and phenyl.

27. A method of claim 21 wherein Z is straight chain alkyl of 1 to 5 carbon atoms.

* * * * *